United States Patent [19]
Baldwin et al.

[11] Patent Number: 5,021,426
[45] Date of Patent: Jun. 4, 1991

[54] METHOD OF TRAETING MALARIA WITH CYPROHEPTADINE DERIVATIVES

[75] Inventors: John J. Baldwin, Gwynedd Valley, Pa.; Gabriel F. Eilon, Irvine, Calif.; Paul A. Friedman, Rosemont; David C. Remy, North Wales, all of Pa.

[73] Assignee: Merck & Co., Inc., Rahway, N.J.

[21] Appl. No.: 484,774

[22] Filed: Feb. 26, 1990

[51] Int. Cl.$^5$ .................... A61K 31/47; A61K 31/445
[52] U.S. Cl. .................... 514/313; 514/314; 514/318; 514/325; 514/895
[58] Field of Search ............... 514/318, 325, 340, 352, 514/313, 314, 895

[56] References Cited

U.S. PATENT DOCUMENTS

| | | | |
|---|---|---|---|
| 3,014,911 | 12/1961 | Engelhardt | 546/203 |
| 4,020,169 | 4/1977 | Remy et al. | 260/328 |
| 4,031,222 | 6/1977 | Remy | 424/267 |
| 4,220,651 | 9/1980 | Remy | 514/325 |
| 4,314,081 | 2/1982 | Molloy et al. | 564/347 |

OTHER PUBLICATIONS

Bitonti et al., *Science*, 242, 1301 (1988), Reversal of Chloroquine Resistance in Malaria Parasite Plasmodium Falciparum by Desipramine.
Foote et al., *Cell*, 57, 921 (1989), Amplification of the Multidrug Resistance Gene in Some Chloroquine Resistant Isolates of P Falciparum.
Higgins, *Nature*, 340, 342 (1989), Export Import Family Expands.
Krogstad et al., *Science*, 238, 1283 (1987), Efflux of Chloroquine from Plasmodium Falciparum, Mechanism of Chloroquine Resistance.
Martin et al., *Science*, 235, 899 (1987), Reversal of Chloroquine Resistance in P. Falciparum by Verapamil.
Randall et al., *J. Med. Chem.*, 22, 1222 (1979), Synthesis, Assignment of Absolute Classification and Receptor Binding Studies Relevant to the Neuroleptic Activity.
Remy et al., *J. Org. Chem.*, 41, 1644 (1976), Trifluoromethythio Copper.
Remy et al., *J. Med. Chem.*, 20, 1013 (19770), Synthesis & Stereospecific Antipsychotic Activity of (−)-1-Cyclopropylmethyl Piperdine.
Clineschmidt, B. V., *J. Pharmacol. Exp. Therapeutics* 208(1):460–467 (1979).

*Primary Examiner*—Glennon H. Hollrah
*Assistant Examiner*—Gary E. Hollinden
*Attorney, Agent, or Firm*—Hesna J. Pfeiffer; Raymond M. Speer; William H. Nicholson

[57] ABSTRACT

Various 3-substituted cyproheptadine derivatives are useful in the treatment of infection by *Plasmodium falciparum* and in the treatment of malaria either as compounds, pharmaceutically acceptable salts, or pharmaceutical composition ingredients in combination with antimalarial agents or compounds. Methods of treating malaria and methods of treating infection by *Plasmodium falciparum* are also described.

11 Claims, No Drawings

METHOD OF TREATING MALARIA WITH CYPROHEPTADINE DERIVATIVES

The present invention is concerned with the compounds (−)-1-cyclopropylmethyl-4-(3-trifluoromethylthio-5H-dibenzo[a,d]cyclohepten-5-ylidene)piperidine, (+)-1-cyclopropylmethyl-4-(3-iodo-5H-dibenzo[a,d]cyclohepten-5-ylidene)piperidine, 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperdinylidene)-5H-dibenzo[a,d]cyclohepten-3-yl)methyl)benzamide and diethyl 1,4-dihydro-2,6-dimethyl-4-(5-(1-methyl-4-piperidinylidene)-5H-dibenzo[a,d]cyclohepten-3-yl)pyridinedicarboxylate and pharmaceutically acceptable salts thereof which are useful in reversing antimalarial resistance in patients afflicted with antimalarial resistant *Plasmodium falciparum*.

BACKGROUND OF THE INVENTION

Annually malaria afflicts an estimated 200 to 300 million people and results in 2 million deaths worldwide. Malaria is a protozoan infection of the blood and liver resulting from the introduction of the parasite into the bloodstream of the individual via the bite of an infected anopheles mosquito, transfusion of infected blood, or injection with a contaminated needle. The life cycle of the malaria parasite includes stages of maturation in liver cells and multiplication/asexual reproduction in the red blood cells. The induced rupture of the red blood cells when the progeny are released and the occlusion of blood vessels due to the parasitized red blood cells may result in symptoms ranging from low-grade fever, chills, headache, malaise and myalgia to severe headache, drowsiness, delerium and acute attacks of fever and chills and may be fatal if left untreated.

Chloroquine, 7-chloro-4-(4-diethylamino-1-methylbutylamino)quinoline, was introduced for the prevention and treatment of malaria over 40 years ago and is currently the most widely used drug in the prophylaxis and treatment of malaria. Though chloroquine is effective against three of the four plasmodium species that cause malaria, certain strains of *Plasmodium falciparum* which are resistant to chloroquine, 4-aminoquinolines and quinolines, in general, have developed in geographic regions where malaria is endemic.

The resistance of these plasmodia is possibly due to a decreased accumulation of chloroquine in the parasite resulting from the rapid efflux of the drug from the resistant parasite. This removal of chloroquine occurs via a putative chloroquine efflux pump, inhibition of which would provide a useful method for allowing accumulation of the antimalarial agent and hence prompting a reversal of the chemical resistance of the parasite.

Chloroquine resistance in *Plasmodia falciparum* shares some of the characteristics of multidrug resistance found in mammalian tumor cells (*Nature*, 340 342 (1989), *Cell*, 57, 921–930 (1989)). It is known that some compounds which reverse multidrug resistance in mammalian tumor cells may also act to reverse chloroquine resistance in *P. falciparum* (*Science*, 235, 899, (1987)). In addition some calcium channel blockers including verapamil and diltiazem inhibit the removal of chloroquine from the plasmodia and reverse chloroquine resistance in vitro and/or in vivo (*Science*, 238, 1283, (1987)).

Desipramine and several tricyclic antidepressant compounds also have the ability to reverse chloroquine resistance and may be useful in combinative therapy with chloroquine in patients infected with chloroquine resistant plasmodium species (*Science*, 242, 1301 (1988)). These antidepressants, in particular desipramine, suffer from the problem that potentially harmful dosages are required to induce remission of chloroquine resistance.

At present, the most preferred method of prophylaxis for chloroquine resistant *P. falciparum* which involves administration of a combination of chloroquine with pyrimethamine and sulfadoxine suffers from the possibility of inducing severe cutaneous reactions in the patient. Likewise, the current treatment for drug-resistant falciparum malaria which involves the concurrent administration of quinine, pyrimethamine, and a sulfonamide (such as sulfadiazine) may result in side effects including tinnitus, drug fever, allergic purpara, and anemia. There remains, therefore, a very real and substantial need for an adjunct therapy to chloroquine administration in the prophylaxis and treatment of chloroquine resistant *P. falciparum* that minimizes potential side effects.

The compounds of this invention being tricyclic compounds are effective in combination with chloroquine for the prophlaxis, suppression therapy, and treatment of chloroquine resistant *P. falciparum*. In addition, the compounds of this invention exhibit a synergistic effect with chloroquine and, hence, are useful in combination therapy against chloroquine resistant malaria parasites.

The present invention has met the above described need by providing a method which preferably involves administering to a person a therapeutically effective dosage of the compound of this invention in combination with or concurrent with the administration of a therapeutically effective dosage of an antimalarial drug either as a prophylaxis for or as direct treatment of drug-resistant malarials. In addition, the compounds of this invention may have a lower propensity to induce extrapyramidal side effects that are experienced with many tricyclic compounds.

SUMMARY OF THE INVENTION

This invention is concerned with the use of the compounds (−)-1-cyclopropylmethyl-4-(3-trifluoromethylthio-5H-dibenzo[a,d]cyclohepten-5-ylidene)piperidine, (+)-1-cyclopropylmethyl-4-(3-iodo-5H-dibenzo[a,d]cyclohepten-5-ylidene)piperidine, 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperidinylidene)-5H-dibenzo[a,d]cyclohepten-3-yl)methyl)benzamide or diethyl 1,4-dihydro-2,6-dimethyl-4-(5-(1-methyl-4-piperidinylidene)-5H-dibenzo[a,d]cyclohepten-3-yl)-pyridinedicarboxylate and pharmaceutically acceptable non-toxic salts thereof, with antimalarial agents in the treatment of infection by *Plasmodium falciparum* and the treatment of malaria.

DETAILED DESCRIPTION OF THE INVENTION

The compounds useful as the active ingredient in the composition of the present invention are:

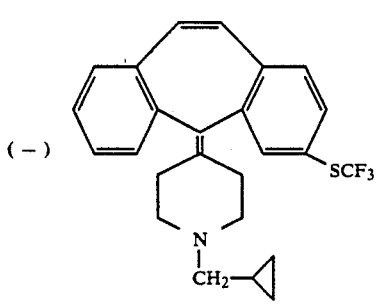

(−)-1-cyclopropylmethyl-4-(3-trifluoromethyl-thio-5H-dibenzo[a,d]cyclohepten-5-ylidene)piperidine;

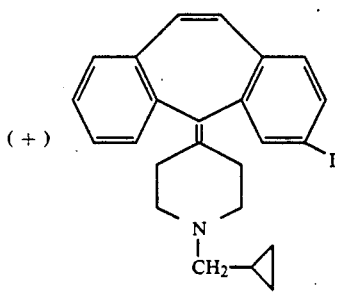

(+)-1-cyclopropylmethyl-4-(3-iodo-5H-dibenzo[a,d]cyclohepten-5-ylidene)piperidine;

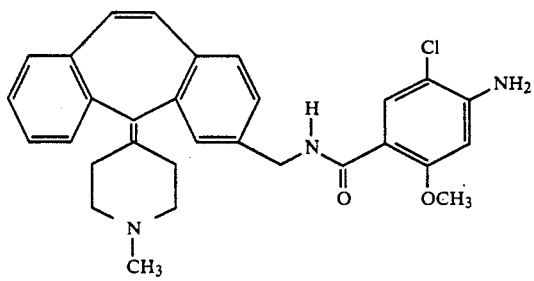

4-amino-5-chloro-2-methoxy-N-((5-(1-methyl-4-piperidinylidene)-5H-dibenzo[a,d]cyclohepten-3-yl)methyl)-benzamide;

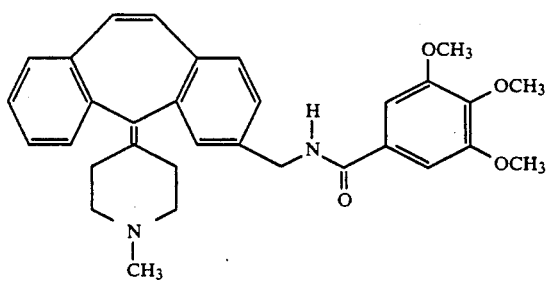

3,4,5-trimethoxy-N-((5-(1-methyl-4-piperidinylidene)-5H-dibenzo[a,d]cyclohepten-3-yl)methyl)benzamide;

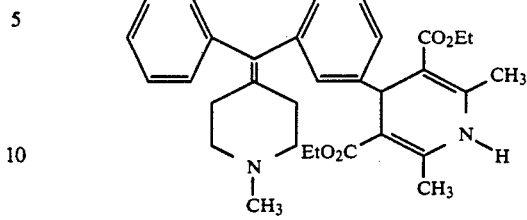

diethyl 1,4-dihydro-2,6-dimethyl-4-(5-(1-methyl-4-piperidinylidene)-5H-dibenzo[a,d]cyclohepten-3-yl)-pyridinedicarboxylate; and pharmaceutically acceptable salts thereof.

The compounds (-)-1-cyclopropylmethyl-4-(3-trifluoromethylthio-5H-dibenzo[a,d]cyclohepten-5-ylidene)piperidine and (+)-1-cyclopropylmethyl-4-(3-iodo-5H-dibenzo[a,d]cyclohepten-5-ylidene)-piperidine are described as substances useful in treating psychoses in U.S. Pat. No. 4,031,222 of David C. Remy, which is incorporated herein by reference.

The preparation and use of 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperidinylidene)-5H-dibenzo[a,d]cyclohepten-3-yl)methyl)benzamide and diethyl 1,4-dihydro-2,6-dimethyl-4-(5-(1-methyl-4-piperidinylidene)-5H-dibenzo[a,d]cyclohepten-3-yl)pyridinedicarboxylate are described herein.

The compounds 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperidinylidene)-5H-dibenzo[a,d]cyclohepten-3-yl)methyl)benzamide and diethyl 1,4-dihydro-2,6-dimethyl-4-(5-(1-methyl-4-piperidinylidene)-5H-dibenzo[a,d]cyclohepten-3-yl)pyridinedicarboxylate are claimed in U.S. Pat. No. 4,996,321, issued Feb. 26, 1991.

The compounds of the present invention are most easily administered in the form of a pharmaceutically acceptable non-toxic acid addition salt formed from the compound and an organic or inorganic acid recognized in the art as providing a pharmaceutically acceptable non-toxic acid addition salt of these compounds which are formed, e.g., from inorganic or organic acids. Examples of such acid addition salts include acetate, aspartate, benzoate, benzenesulfonate, bisulfate, butyrate, citrate, dihydrogen phosphate, dodecylsulfate, ethanesulfonate, fumarate, hydrochloride, hydrobromide, hydroiodide, lactate, maleate, methanesulfonate, 2-naphthalenesulfonate, nicotinate, oxalate, pivalate, pyruvate, propionate, succinate, sulfate, tartrate, thiocyanate, tosylate, maleate, fumarate, or the like. A more preferred embodiment of the invention is that in which a compound is present as the hydrochloride salt.

The novel compounds of the present invention possess activity in reversing chloroquine resistance and are useful as adjuncts to the administration of an antimalarial agent or compound in the prevention and in the treatment of infection by Plasmodium falciparum in a patient in need of such prevention or treatment. For the prevention or the treatment of infection by Plasmodium falciparum a compound of the present invention may be administered in combination with, prior to, concurrent to or subsequent to the administration of an antimalarial agent or compound.

This invention also relates to a method for the reversal of chloroquine resistance in patients afflicted with chloroquine resistant *Plasmodium falciparum* involving the administration to a patient in need of such therapy a pharmaceutical composition comprising a pharmaceutical carrier and a therapeutically-effective amount of a compound of the present invention or a pharmaceutically acceptable acid addition salt thereof.

For these purposes, the compounds of the present invention may be administered (alone or in combination with an antimalarial agent or compound) orally, parenterally (including subcutaneous injections, intravenous, intramuscular, intrasternal injection or infusion techniques) or rectally, in dosage unit formulations containing conventional non-toxic, pharmaceutically-acceptable carriers, adjuvants and vehicles.

The pharmaceutical compositions of this invention can be used in the form of a pharmaceutical preparation, for example, in solid, semisolid or liquid form, which contains one or more of the compounds of the present invention, as an active ingredient, (alone or in combination with an antimalarial agent or compound) in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

As implied earlier, the compounds of this invention may be administered (alone or in combination with an antimalarial agent or compound) by a variety of established methods, including intravenously, intramuscularly, subcutaneously and orally. Since the compunds of the invention exhibit appreciable oral activity, the preferred mode of administration is that in which a compound of this invention is administered orally. The precise mode of administration, however, is left to the discretion of the practitioner.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixers. Compositions intended for oral use may be prepared according to any method known to the art for the manufacture of pharmaceutical compositions and such compositions may contain one or more agents selected from the group consisting of a sweetening agents such as sucrose, lactose, or saccharin, flavoring agents such as peppermint, oil of wintergreen or cherry, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by know techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be (a) a naturally-occuring phosphatide such as lecithin, (b) a condensation product of an alkylene oxide with a fatty acid, for example, polyoxyethylene stearate, (c) a condensation product of an ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbital monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally, occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative such as methyl and propyl parabans, flavoring such as cherry or orange flavor and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are water, Ringer's solution, citrate buffer and isotonic sodium chloride solution. In addition, sterile, fixed oils are conventionally employed as a solvent or suspending medium. For this purpose any bland fixed oil may be employed including synthetic mono-or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants and the like can be incorporated as required.

A compound of the present invention may also be administered in the form of suppositories for rectal administration of the drug. These compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Since an individual patient may present a wide variation in severity of symptoms and each drug has its unique therapeutic characteristics, it is up to the practitioner to determine the patient's response to treatment and vary the dosages accordingly.

In general, the daily oral dose for the reversal of chloroquine resistance in patients afflicted with chloroquine resistant *Plasmodium falciparum* lies within the range of from about 0.5 μg to about 10 mg per kg body weight and, preferably, within the range of from 50 μg to 1 mg per kg body weight and can be administered in up to four times daily. The daily IV dose for the reversal of chloroquine resistance in patients afflicted with chloroquine resistant *Plasmodium falciparum* lies within the range of from about 1 μg to about 10 mg per kg body weight and, preferably, within the range of from 10 μg to 500 μg per kg body weight.

The present invention is also directed to the use of the compounds of this invention with one or more compounds which are useful in preventing and treating malaria selected from the group consisting of 4-aminoquinolines and other quinolines.

For example, the compounds of the present invention can be given in combinations with such compounds (or combinations of such compounds) or salt or other derivative forms thereof as:

4-Aminoquinolines: chloroquine (including the phosphate, hydrochloride and free base forms); hydroxycloroquine; amodiaquine (including the hydrochloride and free base forms);

Other Quinolines: quinine (including the sulfate, dihydrochloride and gluconate forms); mefloquine (including the phosphate, hydrochloride and free base forms).

The present invention is further directed to the use of the compounds of this invention (in combination with a 4-aminoquinoline or other quinoline) with one or more compounds which are also useful in preventing and treating malaria selected from the group consisting of antibiotics, sulfonamides, folic acid antagonists, and other anitmalarial agents.

For example, the compounds of the present invention can be given in combinations with such compounds (or combinations of such compounds) or salt or other derivative forms thereof as:

Antibiotics: tetracycline; doxycycline;

Sulfonamides: sulfadoxine; sulfadiazine;

Folic Acid Antagonists: pyrimethamine; trimethoprim;

Other Compounds: primaquine (including the phosphate, hydrochloride and free base forms); mefloquine; proguanil; dapsone; chloroguanide (including the hydrochloride form); artemisinine.

For the prevention or the treatment of malaria it is preferred that the compounds of the present invention be administered in combination with or concurrent to the administration of chloroquine, chloroquine phosphate or chloroquine hydrochloride.

The weight ratio of a compound of the present invention to the antimalarial agent or compound may be varied and will depend upon the the effective dose of each ingredient. Generally, an effective dose of each will be used. Thus, for example, when a coupound of the present invention is combined with chloroquine, chloroquine hydrochloride or chloroquine phosphate the weight ratio of the compound of the present invention to chloroquine, chloroquine hydrochloride or chloroquine phosphate ranges from about 1:1 to about 1:10,000, preferably about 1:10 to 1:1,000. Combinations of a compound of the present invention and an antimalarial agent or compound will generally also be within the aforementioned range, but in each case, an effective dose of each active ingredient should be used.

In general, the daily oral dose for the use of a compound of the present invention as an adjunct to chloroquine, chloroquine hydrochloride or chloroquine phosphate in the treatment of malaria lies within the range of from about to about 0.5 μg to about 10 mg per kg body weight and, preferably, within the range of from 50 μg to 1 mg per kg body weight and can be administered in up to four times daily. The daily IV dose for the use of a compound of the present invention as an adjunct to chloroquine, chloroquine hydrochloride or chloroquine phosphate treatment of malaria lies within the range of from about 1 μg to about 10 mg per kg body weight and, preferably, within the range of from 10 μg to 500 μg per kg body weight. For the use of a compound of the present invention as an adjunct to chloroquine, chloroquine hydrochloride or chloroquine phosphate in the prophylaxis of malaria, the daily oral dose lies within the range of from about 0.1 μg to 1 mg per kg body weight and, preferably, within the range of from about 1 μg to 500 μg per kg body weight.

The following examples are included to illustrate the use of the compounds of this invention in the preparation of representative dosage forms and the preparation of sterile solutions for use in the treatment of patients with malaria. It is intended that the specification and examples be considered as exemplary only, with the true scope and spirit of the invention being included by the claims of the invention.

EXAMPLE 1

4-Amino-5-chloro-2-methoxy-N-((5-(1-methyl-4-piperidinylidene)-5H-dibenzo[a,d]cyclohepten-3-yl)methyl)benzamide

Step A: Preparation of 1-Methyl-4-(3-aminomethyl-5H-dibenzo[a,d]cycloheptene-5-ylidene)piperidine To a suspension of 0.50 g (0.0125 mol) of lithium aluminum hydride in 30 ml of tetrahydrofuran was added dropwise over 30 minutes a solution of 3.92 g (0.0125 mol) of 1-methyl-4-(3-cyano-5H-dibenzo[a,d]cycloheptene-5-ylidene)piperidine (prepared as described in U.S. Pat. No. 3,988,342 (1976), herein incorporated by reference) in 50 ml of tetrahydrofuran. The mixture was stirred at room temperature for 3 hours and then was heated under reflux for one hour. A saturated solution of Rochelles' salt was added dropwise to the cooled, stirred mixture until a clear colorless organic phase was obtained. The inorganic salts remained as a thick paste on the bottom of the flask. The organic phase was decanted and the inorganic residues were extracted twice with hot toluene. The total organic phases were combined and evaporated to dryness. The residue was purified by chromatography on silica gel using chloroform saturated with ammonia gas as an eluant.

The fractions homogeneous by TLC were pooled and evaporated to give 2.94 g (75%) of 1-methyl-4-(3-aminomethyl-5H-dibenzo[a,d]cycloheptene-5-ylidene)piperidine as an oil. A dihydrochloride salt was prepared and was recrystallized from ethanol-ether, mp 263°–265° C.

Anal. Calcd. for $C_{22}H_{24}N_2 \cdot 2 HCl \cdot 0.5 H_2O$: C, 66.36; H, 6.84; N, 7.04; Cl, 17.81; Found: C, 66.56; H, 7.17; N, 7.03; Cl, 17.51.

Step B: Preparation of 4-Amino-5-chloro-2-methoxy-N-(5-(1-methyl-4-piperidinylidene)-5H-dibenzo[a,d]cyclohepten-3-yl)methyl)benzamide To a solution of 0.6 g (3.2 mmole) of 4-amino-5-chloro-2-methoxybenzoic acid in 15 ml of methylene chloride cooled to −15° C. was added 0.347 g (3.7 mmol) of ethyl chloroformate. The solution was stirred for 30 minutes and 1.0 g (3.2 mmole) of 1-methyl-4-(3-aminomethyl-5H-dibenzo[a,d]cycloheptene-5-ylidene)piperidine in 10 ml of methylene chloride was added. The solution was allowed to stir at room temperature for 2 hours. The solution was washed with 1N sodium hydroxide solution, water, and brine, and then was dried (MgSO$_4$). After filtration, the solvent was removed under reduced pressure to give 4-amino-5-chloro-2-methoxy-N-((5(1-methyl-4-piperidinylidene)-5H-dibenzo[a,d]cyclohepten-3-yl)methyl)benzamide as an amorphous foam.

Anal. Calcd. for $C_{30}H_{30}ClN_3O_2$: C, 72.06; H, 6.05; N, 8.40; Found: C, 71.67; H, 6.16; N, 8.13.

NMR (CDCl$_3$): δ 2.2 (s, N-CH); 2.0–2.5 (m, aliphatic piperidine hydrogens), 3.8 (s, OCH$_3$); 4.4 (s,NH$_2$); 4.6 (d of d CH—NH—); 6.9 (s, CH=CH); 7.1–7.4 (m, ArH); 7.9 (t, —CH$_2$NH—); 8.2 (s, ArH).

EXAMPLE 2

3,4,5-Trimethoxy-N-((5-(1-methyl-4-piperidinylidene)-5H-dibenzo[a,d]cyclohepten-3-yl)methyl)benzamide To a mixture of 0.50 g (1.26 mmol) of the dihydrochloride salt of 1-methyl-4-(3-aminomethyl-5H-dibenzo[a,d]cycloheptene-5-ylidene)piperidine and 0.25 g (1.08 mmol) 3,4,5-trimethoxybenzoyl chloride in 25 ml of toluene was added 1 ml of 10% aqueous sodium hydroxide. The mixture was shaken vigorously for 5 minutes. The toluene was removed by evaporation under reduced pressure and the residual gum was redissolved in chloroform. This chloroform phase was separated, dried over magnesium sulfate, filtered, and the chloroform was removed by evaporation. The crystalline residue was recrystallized from acetonitrile to give 3,4,5-trimethoxy-N-((5-(1-methyl-4-piperidinylidene)-5H-dibenzo[a,d]cyclohepten-3-yl)methyl)benzamide, mp 200°–202° C.

Anal. Calcd. for $C_{32}H_{34}N_2O_4$: C, 75.27; H, 6.71; N, 5.49; Found: C, 75.27; H, 6.92; N, 5.77.

EXAMPLE 3

Diethyl 1,4-dihydro-2,6-dimethyl-4-(5-(1-methyl-4-piperidinylidene)-5H-dibenzo[a,d]cyclohepten-3yl)-pyridine dicarboxylate

Step A: Preparation of 1-Methyl-4-(3-formyl-5H-dibenzo[a,d]cycloheptene-5-ylidene)piperidine A mixture of 1.70 g of 1-methyl-4-(3-cyano-5H-dibenzo[a,d]cycloheptene-5-ylidene)piperidine (prepared as described in U.S. Pat. No. 3,988,342 (1976)), 1.70 g of Raney nickel-aluminum alloy, and 25 ml of 75% aqueous formic acid was stirred under reflux for 1.5 hours. The cooled mixture was filtered and the filtrate was made basic by the additional of solid sodium bicarbonate. Extraction of the neutralized mixture with chloroform and evaporation of the solvent gave 1.30 g of 1-methyl-4-(3-formyl-5H-dibenzo[a,d]cycloheptene-5-ylidene)piperidine.

Step B: Preparation of Diethyl 1,4-dihydro-2,6-dimethyl-4-(5-(1-methyl-4-piperidinylidene)-5H-dibenzo[a,d]cyclohepten-3-yl)-pyridinedicarboxylate A solution of 1.30 g (4.12 mmol) of 1-methyl-4-(3-formyl-5H-dibenzo[a,d]cycloheptene-5-ylidene)piperidine, 1.07 g (8.24 mmol) of ethyl acetoacetate, 0.51 ml of concentrated ammonium hydroxide, and 8 ml of ethanol was stired under reflux for 24 hours. An additional 0.26 g of ethyl acetoacetate and 0.20 ml of concentrated ammonium hydroxide was added, and the solution was reluxed an additional 24 hours.

The solvent was evaporated and the crude product was purified by flash chromatography on silica gel using 10% methanol in chloroform. Evaporation of eluant gave crystalline diethyl 1,4-dihydro-2,6-dimethyl-4-(5-(1-methyl-4-piperidinylidene)-5H-dibenzo[a,d-]cyclohepten-3-yl)pyridine dicarboxylate that was recrystallized from acetonitrile to afford 0.65 g of pure diethyl 1,4-dihydro-2,6-dimethyl-4-(5-(1-methyl-4-piperidinylidene)-5H-dibenzo[a,d]cyclohepten-3-yl)-pyridinedicarboxylate; mp 204°–206° C.

Anal. Calcd. for $C_{34}H_{38}N_2O_4$:C, 75.81; H, 7.11; N, 5.20; Found: C, 75.78; H, 7.31; N,5.60.

EXAMPLE 4

| Dry Filled Capsules Containing 5 mg of Active Ingredient Per Capsule | |
| --- | --- |
| | Per Capsule |
| (-)-1-Cyclopropylmethyl-4-(3-trifluoromethylthio-5H-dibenzo[a,d]cyclohepten-5-ylidene)-piperidine hydrochloride | 5 mg |
| Starch | 88 mg |
| Magnesium stearate | 7 mg |

The (−)-1-cyclopropylmethyl-4-(3-trifluoromethylthio-5H-dibenzo[a,d]cyclohepten-5ylidene)piperidine hydrochloride (5mg) is reduced to a No. 60 powder and then starch (88 mg) and magnesium stearate (7 mg) are passed through a No. 60 bolting cloth onto the powder and the combined ingredients admixed for 10 minutes and then filled into a hard shell capsule of a suitable size at a fill weight of 100 mg per capsule.

Similar dry-filled capsules can be prepared by replacing the active ingredient of the above example by any of the other compounds of this invention.

EXAMPLE 5

| Dry Filled Capsules Containing 5 mg Of Active Ingredient In Combination With 250 mg Chloroquine Phosphate | |
| --- | --- |
| | Per Capsule |
| (-)-1-Cyclopropylmethyl 4-(3-trifluoromethylthio-5H-dibenzo[a,d]cyclohepten-5-ylidene)-piperidine hydrochloride | 5 mg |
| 7-Chloro-4-(4-diethylamino-1-methylbutylamino)quinoline phosphate | 250 mg |
| Lactose, U.S.P | 344 mg |
| Magnesium stearate | 5 mg |

A mixture of 7-chloro-4-(4-diethylamino-1-methyl-butylamino)quinoline phosphate (250 mg) and (−)-1-cyclopropylmethyl-4-(3-trifluoromethylthio-5H-dibenzo[a,d]cyclohepten-5-ylidene)piperidine hydrochloride (5 mg) is reduced to a No. 60 powder and then lactose (344 mg) and magnesium stearate (5 mg) are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other compounds of this invention or by replacing chloroquine phosphate with any other antimalarial agent.

EXAMPLE 6

| Tablets Containing 5 mg Of Active Ingredient | |
| --- | --- |
| | Per Tablet |
| (-)-1-Cyclopropylmethyl 4-(3-trifluoromethylthio-5H-dibenzo[a,d]cyclohepten-5-ylidene) piperidine hydrochloride | 5 mg |
| Corn Starch, U.S.P. | 6 mg |
| Magnesium stearate | 5 mg |
| Dicalcium Phosphate | 252 mg |
| Lactose, U.S.P. | 250 mg |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

Similar tablets can be prepared by replacing the active ingredient of the above example by any of the other compounds of this invention.

EXAMPLE 7

Parenteral Solution of the Hydrochloride Salt of (−)-1-Cyclopropylmethyl-4-(3-trifluromethylthio-5H-dibenzo[a,d]cyclohepten-5-ylidene)piperidine (−)-1-Cyclopropylmethyl-4-(3-trifluoromethylthio-5H-dibenzo[a,d]cyclohepten-5-ylidene)piperidine hydrochloride (1 mg) is dissolved in 1 ml water and sufficient isotonic buffer to make a final volume of 10 ml and the solution is sterilized by filtration. The water from all sources was pyrogen-free.

EXAMPLE 8

Parenteral Solution of the Hydrochloride Salt of 4-Amino-5-chloro-2-methoxy-N-((5-(1-methyl-4-piperidinylidene)-5H-dibenzo[a,d]cyclohepten-3-yl)methyl)benzamide 4-Amino-5-chloro-2-methoxy-N-((5-(1-methyl-4-piperidinylidene)-5H-dibenzo[a,d]cyclohepten-3-yl)methyl)benzamide (1 mg) is dissolved in 1 ml water and sufficient isotonic buffer to make a final volume of 10 ml and the solution is sterilized by filtration. The water from all sources was pyrogen-free.

EXAMPLE 9

Parenteral Solution of the Hydrochloride Salt of 3,4,5-Trimethoxy-N-((5-(1-methyl-4-piperidinylidene)-5H-dibenzo[a,d]cyclohepten-3-yl)methyl)benzamide 3,4,5-Trimethoxy-N-((5-(1-methyl-4-piperidinylidene)-5H-dibenzo[a,d]cyclohepten-3-yl)methyl)benzamide hydrochloride (1 mg) is dissolved in 1 ml water and sufficient isotonic buffer to make a final volume of 10 ml and the solution is sterilized by filtration. The water from all sources was pyrogen-free.

EXAMPLE 10

Parenteral Solution of
(−)-1-Cyclopropylmethyl-4-(3-trifluoromethyl-thio-5H-dibenzo[a,d]cyclohepten-5-ylidene)piperidine Hydrochloride in Combination With Chloroquine Dihydrochloride (−)-1-Cyclopropylmethyl-4-(3-trifluoromethylthio-5H-dibenzo[a,d]cyclohepten-5-ylidene)piperidine hydrochloride (5 mg) and 7-chloro-4-(4-diethylamino-1-methylbutylamino)quinoline dihydrochloride (200 mg) are dissolved in 5 ml water and sufficient isotonic buffer to make a final volume of 10 ml and the solution is sterilized by filtration. The water from all sources was pyrogen-free.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A method of treating a patient afflicted with malaria comprising administering to the patient in need of such treatment a therapeutically effective dose of the cyproheptadine compound which is selected from the group consisting of:

(−)-1-cyclopropylmethyl-4-(3-trifluoromethylthio-5H-dibenzo[a,d]cyclohepten-5-ylidene)piperidine;
(+)-1-cyclopropylmethyl-4-(3-iodo-5H-dibenzo[a,d]cyclohepten-5-ylidene)piperidine;
4-amino-5-chloro-2-methoxy-N-((5-(1-methyl-4-piperidinylidene)-5H-dibenzo[a,d]cyclohepten-3-yl)methyl)benzamide;
3,4,5-trimethoxy-N-((5-(1-methyl-4-piperidinylidene)-5H-dibenzo[a,d]cyclohepten-3-yl)methyl)benzamide;
diethy 1,4-dihydro-2,6-dimethyl-4-(5-(1-methyl-4-piperidinylidene)-5H-dibenzo[a,d]cyclohepten-3-yl)-pyridinedicarboxylate;
or pharmaceutically acceptable acid addition salt thereof, in combination with, prior to, concurrent to or subsequent to the administration of a therapeutically effective dose of the compound which is selected from the group consisting of:
chloroquine; hydroxychloroquine; amodiaquine; mefloquine; or pharmaceutically acceptable acid addition salt thereof.

2. The method of claim 1, wherein said cyproheptadine compound is administered in combination with, prior to, concurrent to or subsequent to the administration of a therapeutically effective dose of chloroquine, chloroquine hydrochloride or chloroquine phosphate.

3. The method of claim 1, wherein said cyproheptadine compound is administered orally.

4. The method of claim 1, wherein said cyproheptadine compound is administered in the form of the hydrochloride salt.

5. A method for the prevention of malaria in a patient which comprises the administration to the patient susceptible to infection by malaria a therapeutically effective dose of the cyproheptadine compound which is selected from the group consisting of:

(−)-1-cyclopropylmethyl-4-(3-trifluoromethylthio-5H-dibenzo[a,d]cyclohepten-5-ylidene)piperidine;
(+)-1-cyclopropylmethyl-4-(3-iodo-5H-dibenzo[a,d]cyclohepten-5-ylidene)piperidine;
4-amino-5-chloro-2-methoxy-N-((5-(1-methyl-4-piperidinylidene)-5H-dibenzo[a,d]cyclohepten-3-yl)methyl)benzamide;
3,4,5-trimethoxy-N-((5-(1-methyl-4-piperidinylidene)-5H-dibenzo[a,d]cyclohepten-3-yl)methyl)benzamide;
diethyl 1,4-dihydro-2,6-dimethyl-4-(5-(1-methyl-4-piperidinylidene)-5H-dibenzo[a,d]cyclohepten-3-yl)-pyridinedicarboxylate;
or pharmaceutically acceptable acid addition salt thereof, in combination with a therapeutically effective dose of the compound which is selected from the group consisting of:
chloroquine; hydroxychloroquine; amodiaquine; mefloquine; or pharmaceutically acceptable acid addition salt thereof.

6. The method of claim 5, wherein said cyproheptadine compound is administered in combination with a therapeutically effective dose of chloroquine, chloroquine hydrochloride or chloroquine phosphate.

7. The method of claim 5, wherein said cyproheptadine compound is administered orally.

8. The method of claim 7, wherein said cyproheptadine compound is administered in the form of the hydrochloride salt.

9. A pharmaceutical composition useful in treating malaria in a patient in need thereof which comprises a mixture of the cyproheptadine compound which is selected from the group consisting of:

(−)-1-cyclopropylmethyl-4-(3-trifluoromethylthio-5H-dibenzo[a,d]cyclohepten-5-ylidene)piperidine;
(+)-1-cyclopropylmethyl-4-(3-iodo-5H-dibenzo[a,d]cyclohepten-5-ylidene)piperidine;
4-amino-5-chloro-2-methoxy-N-((5-(1methyl-4-piperidinylidene)-5H-dibenzo[a,d]cyclohepten-3-yl)methyl)benzamide;
3,4,5-trimethoxy-N-((5-(1-methyl-4-piperidinylidene)-5H-dibenzo[a,d]cyclohepten-3-yl)methyl)benzamide;
diethyl 1,4-dihydro-2,6-dimethyl-4-(5-(1-methyl-4-piperidinylidene)-5H-dibenzo[a,d]cyclohepten-3-yl)-pyridinedicarboxylate;
or pharmaceutically acceptable acid addition salt thereof, in conjunction with chloroquine, chloroquine hydrochloride or chloroquine phosphate and a pharmaceutically acceptable carrier.

10. A pharmaceutical composition of claim 9 wherein said cyproheptadine compound and chloroquine are present in a unitary dosage form.

11. A pharmaceutical composition of claim 9, wherein the weight ratio of the compound which is selected from the group consisting of:

(−)-1-cyclopropylmethyl-4-(3-trifluoromethylthio-5H-dibenzo[a,d]cyclohepten-5-ylidene)piperidine;
(+)-1-cyclopropylmethyl-4-(3-iodo-5H-dibenzo[a,d]cyclohepten-5-ylidene)piperidine;
4-amino-5-chloro-2-methoxy-N-((5-(1-methyl-4-piperidinylidene)-5H-dibenzo[a,d]cyclohepten-3-yl)methyl)benzamide;
3,4,5-trimethoxy-N-((5-(1-methyl-4-piperidinylidene)-5H-dibenzo[a,d]cyclohepten-3-yl)methyl)benzamide;
diethyl 1,4-dihydro-2,6-dimethyl-4-(5-(1-methyl-4-piperidinylidene)-5H-dibenzo[a,d]cyclohepten-3-yl)-pyridinedicarboxylate;
or pharmaceutically acceptable acid addition salt thereof, to the group consisting of chloroquine, chloroquine hydrochloride and chloroquine phosphate ranges from about 1:1 to about 1:10,000.

* * * * *